United States Patent
Kravtchenko

(10) Patent No.: US 7,736,395 B2
(45) Date of Patent: Jun. 15, 2010

(54) COMPOSITION FOR SIMULTANEOUSLY BLEACHING AND DYEING KERATIN FIBERS, COMPRISING AT LEAST ONE DYE CHOSEN FROM ANIONIC AND NONIONIC DYES AND AT LEAST ONE INERT ORGANIC LIQUID

(75) Inventor: Sylvain Kravtchenko, Shanghai (CN)

(73) Assignee: L'Oreal S.A., Paris (FR)

( * ) Notice: Subject to any disclaimer, the term of this patent is extended or adjusted under 35 U.S.C. 154(b) by 92 days.

(21) Appl. No.: 11/476,814

(22) Filed: Jun. 29, 2006

(65) Prior Publication Data

US 2007/0033743 A1 Feb. 15, 2007

Related U.S. Application Data

(60) Provisional application No. 60/696,510, filed on Jul. 6, 2005.

(30) Foreign Application Priority Data

Jun. 29, 2005 (FR) .................................. 05 51813

(51) Int. Cl.
*A61Q 5/10* (2006.01)
(52) U.S. Cl. ........................ 8/405; 8/406; 8/415; 8/435; 8/437; 8/455; 8/463; 8/464; 8/617; 8/637.1; 8/111
(58) Field of Classification Search ..................... 8/405, 8/406, 415, 435, 437, 455, 456, 463, 464, 8/617, 637.1, 107, 111
See application file for complete search history.

(56) References Cited

U.S. PATENT DOCUMENTS

| | | | |
|---|---|---|---|
| 3,578,387 A | 5/1971 | Zviak et al. | |
| 3,915,921 A | 10/1975 | Schlatzer, Jr. | |
| 4,509,949 A | 4/1985 | Huang et al. | |
| 4,823,985 A | 4/1989 | Grollier et al. | |
| 5,595,197 A | 1/1997 | Samain et al. | |
| 5,688,291 A | 11/1997 | Said et al. | |
| 5,792,221 A | 8/1998 | Lagrange et al. | |
| 6,379,401 B1 | 4/2002 | Legrand et al. | |
| 6,537,328 B1 | 3/2003 | Lang et al. | |
| 6,540,791 B1* | 4/2003 | Dias ................. | 8/111 |
| 7,223,294 B2 | 5/2007 | Desenne et al. | |
| 2002/0004957 A1 | 1/2002 | Imperial | |
| 2002/0102225 A1* | 8/2002 | Hess et al. ..................... | 424/62 |
| 2003/0124079 A1 | 7/2003 | Mougin et al. | |
| 2003/0172473 A1 | 9/2003 | Desenne et al. | |
| 2003/0192134 A1 | 10/2003 | Desenne et al. | |
| 2004/0141943 A1 | 7/2004 | Mougin et al. | |
| 2004/0181883 A1* | 9/2004 | Legrand et al. ................. | 8/405 |
| 2004/0205901 A1 | 10/2004 | Cottard et al. | |
| 2005/0011018 A1* | 1/2005 | Greaves et al. ................. | 8/405 |
| 2005/0050650 A1 | 3/2005 | Rollat-Corvol et al. | |
| 2005/0183212 A1 | 8/2005 | Plos | |
| 2005/0191251 A1 | 9/2005 | Kravtchenko et al. | |
| 2005/0257328 A1 | 11/2005 | Sallwey et al. | |
| 2006/0185098 A1 | 8/2006 | Kravtchenko et al. | |
| 2006/0191079 A1 | 8/2006 | Kravtchenko et al. | |
| 2006/0191080 A1 | 8/2006 | Kravtchenko et al. | |

FOREIGN PATENT DOCUMENTS

| | | |
|---|---|---|
| DE | 203 03 559 U1 | 10/2003 |
| EP | 0 173 109 B1 | 3/1986 |
| EP | 0 216 479 B1 | 4/1987 |
| EP | 1048 289 A2 * | 11/2000 |
| FR | 2 586 913 A1 | 3/1987 |
| FR | 2 692 572 A1 | 12/1993 |
| FR | 2 713 926 A1 | 6/1995 |
| FR | 2 773 478 A1 | 7/1999 |
| FR | 2 788 976 A1 | 8/2000 |
| FR | 2 811 993 A1 | 1/2002 |
| FR | 2 820 032 A1 | 8/2002 |
| FR | 2 833 833 A1 | 6/2003 |
| FR | 2 857 587 A1 | 1/2005 |
| FR | 2 864 444 A1 | 7/2005 |
| FR | 2 865 396 A1 | 7/2005 |
| FR | 2 878 741 A1 | 6/2006 |
| FR | 2 878 742 A1 | 6/2006 |
| FR | 2 878 743 A2 | 6/2006 |
| GB | 859 550 | 1/1961 |
| WO | WO 98/44012 | 10/1998 |
| WO | WO 01/28508 A1 | 4/2001 |
| WO | WO 02/074270 A1 | 9/2002 |
| WO | WO 2004/078150 A1 | 9/2004 |

OTHER PUBLICATIONS

English Abstract of the Patent No. EP 1048 289 A1.*
French Search Report for FR 0551812, dated Feb. 17, 2006.
French Search Report for FR 0551813, dated Feb. 23, 2006.
G. Fonnum et al., "Associative thickeners. Part I: Synthesis, rheology and aggregation behavior," Colloid & Polymer Science, vol. 271, No. 4, pp. 380-389 (1993).
Co-pending U.S. Appl. No. 11/476,875, Inventor: Sylvain Kravtchenko, filed Jun. 29, 2006.
Office Action mailed Mar. 18, 2008, in co-pending U.S. Appl. No. 11/476,875.
Final Office Action mailed Dec. 2, 2008, in co-pending U.S. Appl. No. 11/476,875.
Advisory Action mailed Feb. 10, 2009, in co-pending U.S. Appl. No. 11/476,875.

* cited by examiner

*Primary Examiner*—Eisa B Elhilo
(74) *Attorney, Agent, or Firm*—Finnegan, Henderson, Farabow, Garrett & Dunner, L.L.P.

(57) ABSTRACT

The present disclosure relates to a composition for simultaneously bleaching and dyeing keratin fibers, comprising at least one direct dye chosen from anionic dyes, nonionic dyes, and addition salts thereof, with the exception of 7-(6'-methylphenylazo)-1-acetamido-3,6-disulfo-8-hydroxynaphthalene, ortho-nitroanilines substituted meta to the amino group, quinoline and quinoline derivatives, and addition salts thereof, at least one inert organic liquid, at least one peroxygenated salt and at least one alkaline agent. The disclosure also relates to a process for simultaneously bleaching and dyeing keratin fibers using this composition.

17 Claims, No Drawings

COMPOSITION FOR SIMULTANEOUSLY BLEACHING AND DYEING KERATIN FIBERS, COMPRISING AT LEAST ONE DYE CHOSEN FROM ANIONIC AND NONIONIC DYES AND AT LEAST ONE INERT ORGANIC LIQUID

This application claims benefit of U.S. Provisional Application No. 60/696,510, filed Jul. 6, 2005, the contents of which are incorporated herein by reference. This application also claims benefit of priority under 35 U.S.C. §119 to French Patent Application No. FR 05 51813, filed Jun. 29, 2005, the contents of which are also incorporated herein by reference.

The present disclosure relates to a composition for simultaneously bleaching and dyeing keratin fibers, including human keratin fibers such as the hair.

When a person wishes to radically change hair color, for example, when he wishes to obtain a color lighter than his original color, it is often necessary to perform bleaching and optionally dyeing of the hair. Several methods are available to do this.

One method consists of using lightening products based on aqueous ammonia and hydrogen peroxide. These products may optionally contain dyes allowing the hair to be simultaneously lightened and dyed. However, the lightening performance of these products remains limited, for example, to applications on natural and/or dyed dark-colored hair.

Another method consists of applying to the hair a lightening composition based on peroxygenated salts such as persulfates and alkaline agents to which has been added hydrogen peroxide at the time of use, in order to obtain greater lightening. This type of product is very satisfactory and more suited to dark hair, but gives access to only a very limited range of tints. It is then necessary to correct the shade obtained by applying to the hair a coloring product in a second stage. This two-stage process can have the drawback of being relatively long.

To overcome this drawback, it has been proposed, in U.S. Pat. No. 5,688,291, International Patent Application No. WO 02/074270 and German Patent Utility Model DE 203 03 559, to add dyes to these lightening products, such as direct dyes of anthraquinone, azo, triarylmethane, thiazine, quinone and nitro type, some of which are stable in these highly oxidative media. This method allows hair fibers to be simultaneously dyed and bleached. Since the level of lightening is substantial, it is suitable, for example, for natural and/or dyed dark-colored hair. However, these products have the drawback of being in the form of powders that can be volatile and of reduced practicality.

Accordingly, the present disclosure relates to novel compositions for simultaneously bleaching and dyeing keratin fibers, including human keratin fibers such as the hair, which may be, for example, suitable for dark-colored hair, which may be easy to use and which can produce chromatic and fast colorations.

Thus, one aspect of the present disclosure, a composition is disclosed for simultaneously bleaching and dyeing keratin fibers, comprising:
  at least one direct dye chosen from anionic dyes, nonionic dyes, and addition salts thereof, with the exception of 7-(6'-methylphenylazo)-1-acetamido-3,6-disulfo-8-hydroxynaphthalene, ortho-nitroanilines substituted meta to the amino group, quinoline, quinoline derivatives, and addition salts thereof;
  at least one inert organic liquid;
  at least one peroxygenated salt; and
  at least one alkaline agent.

The composition in accordance with the present disclosure may be suitable, for example, for simultaneously bleaching and dyeing dark hair and may be easy to use. Furthermore, the dyes can show good stability in the composition in accordance with the present disclosure. The coloration obtained is chromatic and, with suitable concentrations of dyes according to the present disclosure, a wide range of colors and tints can be obtained.

Moreover, this coloration may withstand the various attacking factors to which the hair may be subjected, such as shampoo, rubbing, light, bad weather, sweat and permanent reshaping. It can also be powerful, aesthetic and, furthermore, sparingly selective, i.e., it may produce small differences in color between different parts, which are differently sensitized, of a hair or of a head of hair.

The present disclosure also relates to a process for simultaneously bleaching and dyeing keratin fibers using the composition in accordance with the present disclosure, and also multi-compartment devices or "kits" for performing this process.

Another aspect of the present disclosure relates to the use of the composition in accordance with the present disclosure for simultaneously bleaching and dyeing keratin fibers.

The anionic dyes that may be used in the context of the disclosure may be chosen from acidic nitro direct dyes, acidic azo dyes, acidic azine dyes, acidic triarylmethane dyes, acidic indoamine dyes and acidic natural dyes.

In at least one embodiment, the anionic dyes that may be used in the context of the disclosure are chosen from the following compounds:

| | |
|---|---|
| (C.I. 45380) | Acid Red 87 |
| (C.I. 10316) | Sodium salt of 2,4-dinitro-1-naphthol-7-sulfonic acid |
| (C.I. 10383) | Acid Orange 3 |
| (C.I. 13015) | Acid Yellow 9/Food Yellow 2 |
| (C.I. 14780) | Direct Red 45/Food Red 13 |
| (C.I. 13711) | Acid Black 52 |
| (C.I. 13065) | Acid Yellow 36 |
| (C.I. 14700) | Sodium salt of 1-hydroxy-2-(2',4'-xylyl-5-sulfonatoazo)naphthalene-4-sulfonic acid/Food Red 1 |
| (C.I. 14720) | Acid Red 14/Food Red 3/Mordant Blue 79 |
| (C.I. 14805) | Acid Brown 4 |
| (C.I. 15510) | Acid Orange 7/Pigment Orange 17/Solvent Orange 49 |
| (C.I. 15985) | Food Yellow 3/Pigment Yellow 104 |
| (C.I. 16185) | Acid Red 27/Food Red 9 |
| (C.I. 16230) | Acid Orange 10/Food Orange 4 |
| (C.I. 16250) | Acid Red 44 |
| (C.I. 17200) | Acid Red 33/Food Red 12 |
| (C.I. 15685) | Acid Red 184 |
| (C.I. 19125) | Acid Violet 3 |
| (C.I. 18055) | Sodium salt of 1-hydroxy-2-(4'-acetamidophenylazo)-8-acetamidonaphthalene-3,6-disulfonic acid/Acid Violet 7/Food Red 11 |
| (C.I. 18130) | Acid Red 135 |
| (C.I. 19130) | Acid Yellow 27 |
| (C.I. 19140) | Acid Yellow 23/Food Yellow 4 |
| (C.I. 20170) | 4'-(Sulfonato-2",4"-dimethyl)bis(2,6-phenylazo)-1,3-dihydroxybenzene/Acid Orange 24 |
| (C.I. 20470) | Sodium salt of 1-amino-2-(4'-nitrophenylazo)-7-phenylazo-8-hydroxynaphthalene-3,6-disulfonic acid/Acid Black 1 |
| (C.I. 23266) | (4-((4-Methylphenyl)sulfonyloxy)phenylazo)-2,2'-dimethyl-4-((2-hydroxy-5,8-disulfonato)naphthylazo)biphenyl/Acid Red 111 |
| (C.I. 27755) | Food Black 2 |
| (C.I. 25440) | 1-(4'-Sulfonatophenylazo)-4-((2"-hydroxy-3"-acetylamino-6",8"-disulfonato)naphthylazo)-6-sulfonatonaphthalene (tetrasodium salt)/Food Black 1 |
| (C.I. 42080) | 4-β-Hydroxyethylamino-3-nitrobenzenesulfonic acid |
| (C.I. 42090) | Acid Blue 9 |
| (C.I. 60730) | Acid Violet 43 |
| (C.I. 61570) | Acid Green 25 |
| (C.I. 62045) | Sodium salt of 1-amino-4-cyclohexylamino-9,10-anthraquinone-2-sulfonic acid/Acid Blue 62 |
| (C.I. 62105) | Acid Blue 78 |

-continued

| | |
|---|---|
| (C.I. 14710) | Sodium salt of 4-hydroxy-3-((2-methoxyphenyl)azo)-1-naphthalenesulfonic acid/Acid Red 4 |
| | 2-Piperidino-5-nitrobenzenesulfonic acid |
| | 2-(4'-N,N-(2''-Hydroxyethyl)amino-2'-nitro)-anilinethanesulfonic acid |
| | 4-β-Hydroxyethylamino-3-nitrobenzenesulfonic acid |
| (C.I. 42640) | Acid Violet 49 |
| (C.I. 42080) | Acid Blue 7 |
| — | Acid Blue 156 |
| — | Acid Blue 317 |
| (C.I. 58005) | Sodium salt of 1,2-dihydroxy-3-sulfoanthraquinone/ Mordant Red 3 |
| (C.I. 62055) | Sodium salt of 1-amino-9,10-dihydro-9,10-dioxo-4-(phenylamino)-2-anthracenesulfonic acid/Acid Blue 25 |
| (C.I. 14710) | Sodium salt of 4-hydroxy-3-((2-methoxyphenyl)azo)-1-naphthalenesulfonic acid/Acid Red 4 |

Most of these dyes are described, for example, in the Color Index published by The Society of Dyers and Colorists, P.O. Box 244, Perkin House, 82 Grattan Road, Bradford, Yorkshire, BD1 2JB, England.

In another embodiment, the anionic dyes may be chosen from, for example, the dyes designated in the Color Index under the code C.I. 58005 (monosodium salt of 1,2-dihydroxy-9,10-anthraquinone-3-sulfonic acid), C.I. 60730 (monosodium salt of 2-[(9,10-dihydro-4-hydroxy-9,10-dioxo-1-anthracenyl)amino]-5-methylbenzenesulfonic acid), C.I. 15510 (monosodium salt of 4-[(2-hydroxy-1-naphthyl)azo]benzenesulfonic acid), C.I. 15985 (disodium salt of 6-hydroxy-5-[(4-sulfophenyl)azo]-2-naphthalenesulfonic acid), C.I. 17200 (disodium salt of 5-amino-4-hydroxy-3-(phenylazo)-2,7-naphthalenedisulfonic acid), C.I. 20470 (disodium salt of 1-amino-2-(4'-nitrophenylazo)-7-phenylazo-8-hydroxynaphthalene-3,6-disulfonic acid), C.I. 42090 (disodium salt of N-ethyl-N-[4-[[4-[ethyl(3-sulfophenyl)methyl] amino]phenyl](2-sulfophenyl)methylene]-2,5-cyclohexadien-1-ylidene]-3-sulfobenzenemethanaminium hydroxide, inner salt) and C.I. 61570 (disodium salt of 2,2'-[(9,10-dihydro-9,10-dioxo-1,4-anthracenediyl)diimino]bis[5-methyl]benzenesulfonic acid).

In a further embodiment, the at least one anionic dyes that may be used according to the present disclosure may also be chosen from the following compounds:
4-(β-hydroxyethyl)amino-3-nitrobenzenesulfonic acid;
4-N-ethylamino-3-nitrobenzoic acid;
2-piperidino-5-nitrobenzoic acid;
4-amino-2-nitrodiphenylamine-2'-carboxylic acid;
4-amino-4'-dimethylamino-2-nitrodiphenylamine-2'-carboxylic acid; and
3-oxo-6-hydroxy-9-carboxyphenylxanthylium acid.

The at least one nonionic dye that may be used according to at least one embodiment of the present disclosure may be chosen from nonionic nitrobenzene dyes, nonionic azo, azomethine, methine, anthraquinone, naphthoquinone, benzoquinone, phenothiazine, indigoid, xanthene, phenanthridine, phthalocyanin and triarylmethane-based dyes.

The at least one nonionic dye may be chosen, for example, from red or orange nitrobenzene dyes, for example the following compounds:
1-hydroxy-3-nitro-4-N-(γ-hydroxypropyl)aminobenzene,
N-(β-hydroxyethyl)amino-3-nitro-4-aminobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene, and
2-nitro-4'-hydroxydiphenylamine.

The nonionic dyes may also be chosen from yellow and green-yellow nitrobenzene direct dyes, such as the following compounds:
1-(β-hydroxyethyl)amino-2-methoxy-4-nitrobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

The nonionic dyes may also be chosen from blue and violet nitrobenzene direct dyes. Non-limiting examples that may be mentioned include the following compounds:
1-(β-hydroxyethyl)amino-4-N,N-bis(β-hydroxyethyl)amino-2-nitrobenzene,
1-(γ-hydroxypropyl)amino-4-N,N-bis(β-hydroxyethyl)amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene, and
the 2-nitro-para-phenylenediamines having the following formula:

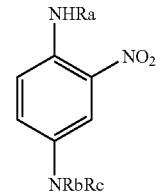

wherein:
Rb is chosen from $C_1$-$C_4$ alkyl radicals, β-hydroxyethyl, β-hydroxypropyl and γ-hydroxypropyl radicals;
Ra and Rc, which may be identical or different, are chosen from β-hydroxyethyl, β-hydroxypropyl, γ-hydroxypropyl and β,γ-dihydroxypropyl radicals; wherein at least one of the radicals Rb, Rc and Ra is a γ-hydroxypropyl radical, with the proviso that Rb and Rc do not simultaneously denote a β-hydroxyethyl radical when Ra is a γ-hydroxypropyl radical, such as those described in French Patent No. FR 2 692 572.

Nonionic dyes that may also be mentioned in a non-limiting manner include the following dyes: Disperse Orange 3; Disperse Red 17; Disperse Violet 4; Disperse Violet 8; Disperse Blue 1; Disperse Red 15; Solvent Violet 13; Solvent Violet 11; Disperse Blue 3; Disperse Blue 7; Disperse Red 11;

Natural Brown 7; Disperse Black 9; Disperse Violet 15; Natural Orange 6; 2-hydroxy-3-methoxy-1,4-naphthoquinone; 3-hydroxy-2-methyl-1,4-naphthoquinone or phthiocol; 3,6-dihydroxy-5-methoxy-p-toluquinone or spinulosin; and HC Blue 14.

In at least one embodiment, the at least one nonionic dye is chosen from 1-hydroxy-3-nitro-4-N-(γ-hydroxypropyl)aminobenzene; N-(β-hydroxyethyl)amino-3-nitro-4-aminobenzene; 1-hydroxy-3-nitro-4-N-(β-hydroxyethyl)aminobenzene; 1,4-diamino-2-nitrobenzene; 1-amino-2-nitro-4-methylaminobenzene; N-(β-hydroxyethyl)-2-nitro-paraphenylenediamine; 2-nitro-4-aminodiphenylamine; 1-amino-3-nitro-6-hydroxybenzene; 1-(β-aminoethyl)amino-2-nitro-4-(β-hydroxyethyloxy)benzene; 1-(β,γ-dihydroxypropyl)oxy-3-nitro-4-(β-hydroxyethyl)aminobenzene; 1-hydroxy-3-nitro-4-aminobenzene; 1-hydroxy-2-amino-4,6-dinitrobenzene; 1-methoxy-3-nitro-4-(β-hydroxyethyl)aminobenzene; 2-nitro-4'-hydroxydiphenylamine; 1-(β-hydroxyethyl)amino-2-methoxy-4-nitrobenzene; 1-amino-2-nitro-6-methylbenzene; 1-(β-hydroxyethyl)amino-2-hydroxy-4-nitrobenzene; N-(β-hydroxyethyl)-2-nitro-4-trifluoromethylaniline; 4-(β-hydroxyethyl)amino-3-nitrochlorobenzene; (4-β-hydroxyethyl)amino-3-nitromethylbenzene; 4-(β,γ-dihydroxypropyl)amino-3-nitrotrifluoromethyl-benzene; 1-(β-ureidoethyl)amino-4-nitrobenzene; 1-hydroxy-2-amino-5-nitrobenzene; 1-amino-2-[tris(hydroxymethyl)methyl]amino-5-nitrobenzene; 1-(β-hydroxyethyl)amino-2-nitrobenzene; 4-(β-hydroxyethyl)amino-3-nitrobenzamide; 1-(β-hydroxyethyl)amino-4-N,N-bis(β-hydroxyethyl)amino-2-nitrobenzene; 1-(γ-hydroxypropyl)amino-4-N,N-bis(β-hydroxyethyl)amino-2-nitrobenzene; 1-(β-hydroxyethyl)amino-4-(N-methyl-N-β-hydroxyethyl)amino-2-nitrobenzene; 1-(β-hydroxyethyl)amino-4-(N-ethyl-N-β-hydroxyethyl)amino-2-nitrobenzene; 1-(β,γ-dihydroxypropyl)amino-4-(N-ethyl-N-β-hydroxyethyl)amino-2-nitrobenzene; Disperse Orange 3; Disperse Red 17; Disperse Violet 4; Disperse Violet 8; Disperse Blue 1; Disperse Red 15; Solvent Violet 13; Solvent Violet 11; Disperse Blue 3; Disperse Blue 7; Disperse Red 11; Natural Brown 7; Disperse Black 9; Disperse Violet 15; Natural Orange 6; 2-hydroxy-3-methoxy-1,4-naphthoquinone; 3-hydroxy-2-methyl-1,4-naphthoquinone or phthiocol; 3,6-dihydroxy-5-methoxy-p-toluquinone or spinulosin; and HC Blue 14.

In at least one embodiment, the concentration of the anionic and/or nonionic dyes in the composition in accordance with the disclosure may range from 0.0001% to 10% by weight, such as, for example, from 0.001% to 8% or from 0.01% to 5% by weight, relative to the total weight of the composition.

For the purposes of the present disclosure, the term "liquid phase" means any phase capable of flowing at room temperature, e.g., from 15° C. to 40° C., and at atmospheric pressure, under the action of its own weight.

For the purposes of the present disclosure, the term "inert organic liquid" means an organic liquid that is chemically inert with respect to hydrogen peroxide. In the context of the disclosure, a liquid is inert if the degradation of hydrogen peroxide in the presence of this liquid is less than 25% after 15 hours at 100° C.

Non-limiting examples of inert organic liquids that may be mentioned include the polydecenes of formula $C_{10n}H_{[(20n)+2]}$ wherein n ranges from 3 to 9, for example from 3 to 7, esters of fatty alcohols and of fatty acids, sugar esters and diesters of $C_{12}$-$C_{24}$ fatty acids, cyclic ethers or cyclic esters, silicone oils, mineral oils and plant oils, and mixtures thereof.

The compounds of formula $C_{10n}H_{[(20n)+2]}$ wherein n ranges from 3 to 9 correspond to the name "polydecene" of the CTFA dictionary, 7th edition, 1997 of the Cosmetic, Toiletry and Fragrance Association, USA, and also to the same INCI name in the USA and in Europe. These are poly-1-decene hydrogenation products.

In at least one embodiment, the composition of the present disclosure comprises a compound of $C_{10n}H_{[(20n)+2]}$ wherein n ranges from 3 to 7.

Non-limiting examples that may be mentioned include the products sold under the name Silkflo® 366 NF Polydecene by the company Amoco Chemical, and those sold under the name Nexbase® 2002 FG, 2004 FG, 2006 FG and 2008 FG by the company Fortum.

Among esters of fatty alcohols or of fatty acids, non-limiting examples that may be mentioned include:

esters of saturated, linear or branched $C_3$-$C_6$ lower monoalcohols with monofunctional $C_{12}$-$C_{24}$ fatty acids, these fatty acids possibly being linear or branched, saturated or unsaturated and chosen, for example, from oleates, laurates, palmitates, myristates, behenates, cocoates, stearates, linoleates, linolenates, caprates and arachidonates, or mixtures thereof, including, for example, oleo-palmitates, oleo-stearates and palmito-stearates. In at least one embodiment of the present disclosure, the composition comprises an ester chosen from isopropyl palmitate, isopropyl myristate and octyldodecyl stearate, esters of linear or branched $C_3$-$C_8$ monoalcohols with difunctional $C_8$-$C_{24}$ fatty acids, these fatty acids possibly being linear or branched, and saturated or unsaturated, for instance the isopropyl diester of sebacic acid, also known as diisopropyl sebacate, esters of linear or branched $C_3$-$C_8$ monoalcohols with difunctional $C_2$-$C_8$ fatty acids, these fatty acids possibly being linear or branched, and saturated or unsaturated, for instance dioctyl adipate and dicaprylyl maleate, and the ester of a trifunctional acid, for instance triethyl citrate.

In the sugar esters and diesters of $C_{12}$-$C_{24}$ fatty acids used according to the present disclosure, the term "sugar" means compounds containing several alcohol functional groups, with or without an aldehyde or ketone functional group, and which comprise at least 4 carbon atoms. These sugars may be monosaccharides, oligosaccharides or polysaccharides.

As sugars that may be used according to the disclosure, non-limiting examples that may be mentioned include sucrose (or saccharose), glucose, galactose, ribose, fucose, maltose, fructose, mannose, arabinose, xylose and lactose, and derivatives thereof, for example, alkyl derivatives such as methyl derivatives, for instance methylglucose.

The sugar esters of fatty acids that may be used according to at least one embodiment of the present disclosure may be chosen from the group comprising esters or mixtures of esters of sugars described above and of linear or branched, saturated or unsaturated $C_{12}$-$C_{24}$ fatty acids.

The esters may be chosen from mono-, di-, tri-, tetraesters and polyesters, and mixtures thereof.

These esters may be chosen, for example, from oleates, laurates, palmitates, myristates, behenates, cocoates, stearates, linoleates, linolenates, caprates and arachidonates, or mixtures thereof such as, for example, oleo-palmitate, oleo-stearate and palmito-stearate mixed esters.

In at least one embodiment of the present disclosure, the esters are chosen from monoesters and diesters and, for example, sucrose, glucose or methylglucose mono- or dioleates, stearates, behenates, oleopalmitates, linoleates, linolenates and oleostearates.

An example that may be mentioned is the product sold under the name Glucate® DO by the company Amerchol, which is a methylglucose dioleate.

Non-limiting examples of esters or mixtures of esters of sugar and of fatty acid that may also be mentioned include:

the products sold under the names F160, F140, F110, F90, F70 and SL 40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name Ryoto Sugar Esters, for example referenced B370 and corresponding to sucrose behenate formed from 20% monoester and 80% diester, triester and polyester;

the sucrose mono-dipalmito-stearate sold by the company Goldschmidt under the name Tegosoft® PSE.

Among examples of cyclic ethers and cyclic esters, γ-butyrolactone, dimethyl isosorbide and diisopropyl isosorbide may be used in at least one embodiment of the present disclosure.

Silicone oils may also be used as the at least one inert organic liquid.

Silicone oils that may be used according to at least one embodiment of the present disclosure are liquid, non-volatile silicone fluids with a viscosity of less than or equal to 10,000 mPa·s at 25° C., the viscosity of the silicones being measured according to ASTM standard 445 Appendix C.

Silicone oils are defined in greater detail in Walter Noll's "Chemistry and Technology of Silicones" (1968)—Academic Press.

Among the silicone oils that may be used according to at least one embodiment of the present disclosure, non-limiting mention may be made of the silicone oils sold under the names DC-200 Fluid—5 mPa·s, DC-200 Fluid—20 mPa·s, DC-200 Fluid—350 mPa·s, DC-200 Fluid—1000 mPa·s and DC-200 Fluid—10,000 mPa·s by the company Dow Corning.

Mineral oils may also be used as the at least one inert organic liquid, for instance liquid paraffin.

Plant oils may also be suitable for use as the at least one inert organic liquid in compositions of the present disclosure, such as, for example, avocado oil, olive oil or liquid jojoba wax.

In at least one embodiment of the present disclosure, the at least one inert organic liquid may be chosen from polydecenes of formula $C_{10n}H_{[(20n)+2]}$ wherein n ranges from 3 to 9, for example from 3 to 7, and esters of fatty alcohols or of fatty acids, and mixtures thereof.

In at least one embodiment of the present disclosure, the at least one inert organic liquid may be present in an amount ranging from 5% to 60% by weight, such as, for example, from 10% to 50% by weight or from 15% to 45% by weight, relative to the weight of the anhydrous paste.

In at least one embodiment, the composition in accordance with the present disclosure may be in paste form.

At least one peroxygenated salt that may be used according to the present disclosure may be chosen, for example, from alkali metal or alkaline-earth metal persulfates, perborates, percarbonates and peroxides, and mixtures thereof. In at least one embodiment, persulfates and mixtures thereof may be used, including, for example, sodium, potassium and ammonium persulfates, and mixtures thereof.

The concentration of peroxygenated salts in the composition in accordance with at least one embodiment of the present disclosure ranges from 1% to 70% by weight, such as, for example, from 20% to 60% by weight relative to the total weight of the composition.

According to at least one embodiment, the at least one alkaline agent that may be used in the composition of the present disclosure can be chosen, for example, from urea, ammonium salts, for instance ammonium chloride, ammonium sulfate, ammonium phosphate and ammonium nitrate, and silicates, phosphates and carbonates of alkali metals and of alkaline-earth metals such as lithium, sodium, potassium, magnesium, calcium and barium. In another embodiment, the at least one alkaline agent may be chosen, for example, from ammonium chloride and silicates and carbonates.

According to at least one embodiment, the alkaline agents can be present in the composition in accordance with the present disclosure in an amount ranging from 0.01% to 40% by weight, such as, for example, from 0.1% to 30% by weight, relative to the total weight of the composition.

According to at least one embodiment, the composition in accordance with the present disclosure is anhydrous.

In the context of the present disclosure, a composition is anhydrous when it has a water content of less than 1% by weight, such as, for example, less than 0.5% by weight, relative to the total weight of the composition.

According to another embodiment of the present disclosure, the composition in accordance with the disclosure is aqueous. It may then also comprise hydrogen peroxide.

In this case, the composition in accordance with the present disclosure is ready to use and results from the mixing of an anhydrous composition in accordance with the disclosure with an aqueous composition optionally comprising hydrogen peroxide. In at least one embodiment, the pH may range from 3 to 11, for example from 7 to 11.

The composition in accordance with the present disclosure may also comprise various additives conventionally used in cosmetics.

The composition in accordance with the present disclosure may thus comprise at least one additional cosmetic adjuvant chosen from mineral and organic thickeners, such as associative or non-associative, anionic, cationic, nonionic or amphoteric thickening polymers, fillers such as clays, binders such as vinylpyrrolidone, lubricants, for instance polyol stearates or alkali metal or alkaline-earth metal stearates, hydrophilic or hydrophobic silicas, pigments, dyes other than those of the present disclosure, matting agents, for instance titanium oxides or anionic, nonionic, cationic, amphoteric or zwitterionic surfactants, antioxidants, penetrants, sequestrants, buffers, dispersants, film-forming agents, preserving agents, opacifiers, vitamins, fragrances, anionic, cationic, nonionic, amphoteric or zwitterionic polymers, ceramides, and conditioning agents, for instance volatile or non-volatile, modified or unmodified silicones.

When the composition in accordance with the present disclosure comprises hydrogen peroxide, it may also comprise at least one agent for controlling the release of oxygen, such as magnesium carbonate or oxide.

The at least one adjuvant and the at least one agent for controlling the release of oxygen as defined above may be present in an amount for each ranging from 0.01% to 40% by weight, such as, for example, from 0.1% to 30% by weight, relative to the total weight of the composition.

Needless to say, a person skilled in the art will take care to select this or these optional additional compounds such that the beneficial properties intrinsically associated with the composition in accordance with the present disclosure are not, or are not substantially, adversely affected by the envisaged addition(s).

The simultaneous bleaching and dyeing process in accordance with the present disclosure comprises applying to keratin fibers an anhydrous composition in accordance with the present disclosure as defined above in the presence of an aqueous composition optionally comprising hydrogen peroxide. The aqueous composition optionally comprising hydrogen peroxide may be added to the anhydrous composition just at the time of use. It may also be applied simultaneously with or sequentially to the anhydrous composition.

Another aspect of the present disclosure relates to a multi-compartment device or kit, which contains at least two compositions, the mixing of which leads to an aqueous composition in accordance with the present disclosure as defined above.

According to at least one embodiment of the present disclosure, the device comprises at least one first compartment that contains a composition (A) comprising, in a suitable dyeing medium, at least one direct dye chosen from anionic and nonionic dyes, and at least one inert organic liquid as defined above, at least one second compartment that contains an anhydrous composition (B) comprising at least one peroxygenated salt and at least one alkaline agent as defined above, and at least one third compartment that contains an aqueous hydrogen peroxide composition (C).

According to another embodiment of the present disclosure, the device comprises at least one first compartment that contains a composition (D) comprising, in a suitable dyeing medium, at least one direct dye chosen from anionic and nonionic dyes as defined above, at least one second compartment that contains an anhydrous composition (E) comprising at least one inert organic liquid, at least one peroxygenated salt and at least one alkaline agent as defined above, and at least one third compartment that contains an aqueous hydrogen peroxide composition (C).

According to yet another embodiment of the present disclosure, the device comprises at least one first compartment that contains an anhydrous composition (F) comprising at least one direct dye chosen from anionic and nonionic dyes, at least one inert organic liquid, at least one peroxygenated salt and at least one alkaline agent as defined above, and at least one second compartment that contains an aqueous hydrogen peroxide composition (C).

According to another embodiment of the present disclosure, the device comprises at least one first compartment that contains an anhydrous composition (E) comprising at least one inert organic liquid, at least one peroxygenated salt and at least one alkaline agent as defined above, and at least one second compartment that contains a composition (G) comprising, in a suitable dyeing medium, at least one direct dye chosen from anionic and nonionic dyes as defined above and hydrogen peroxide.

According to yet another embodiment of the disclosure, the device comprises at least one first compartment that contains an anhydrous composition (B) comprising at least one peroxygenated salt and at least one alkaline agent as defined above, and at least one second compartment that contains a composition (H) comprising, in a suitable dyeing medium, at least one direct dye chosen from anionic and nonionic dyes and at least one inert organic liquid as defined above and hydrogen peroxide.

The suitable dyeing medium for the compositions (A), (C), (D), (G) and (H) may comprise, for example, water or a mixture of water and at least one organic solvent to dissolve the compounds that are not sufficiently water-soluble. Examples of organic solvents that may be mentioned include $C_1$-$C_4$ lower alkanols such as ethanol and isopropanol; glycerol; glycols and glycol ethers, for instance 2-butoxyethanol, propylene glycol and propylene glycol monomethyl ether, and also aromatic alcohols, for instance benzyl alcohol or phenoxyethanol, similar products and mixtures thereof.

In at least one embodiment, the at least one solvent may be present in an amount ranging from 1% to 40% by weight, such as, for example, from 5% to 30% by weight, relative to the total weight of the dye composition.

Compositions (A) and (D), also known as "booster", may be formulated at acidic, neutral or alkaline pH, the pH possibly ranging from 3 to 12, for example from 4 and 11 approximately.

In at least one embodiment of the present disclosure, compositions (C), (G) and (H) may have a pH of less than 7, the acidic pH ensuring the stability of the hydrogen peroxide in this composition.

Compositions (A), (C), (D), (G) and (H) may be in various forms, such as in the form of liquids, creams or gels, or in any other form that is suitable for dyeing keratin fibers.

The anhydrous compositions (E) and (F) may be in paste form.

The anhydrous composition (B) may be in powder or paste form. When it is in the form of paste, it also comprises at least one inert organic liquid as defined above.

Compositions (A) to (I) may also contain at least one adjuvant conventionally used in cosmetics, such as those described above.

Compositions (C), (G) and (H) may also comprise at least one agent for controlling the release of oxygen as defined above.

The device in accordance with the present disclosure may be equipped with an applicator for applying the desired mixture to the hair, such as the devices described in French Patent No. FR-2 586 913.

Using this device, it is possible to simultaneously bleach and dye keratin fibers via a process in accordance with the disclosure as defined above.

Another aspect of the present disclosure relates to the use, for simultaneously bleaching and dyeing keratin fibers, of a composition in accordance with the present disclosure as defined above.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in its respective testing measurement.

The examples that follow serve to illustrate the present disclosure without, however, being limiting in nature.

EXAMPLES

The compositions below were prepared:

|  | Composition (bleaching paste) | | |
|---|---|---|---|
|  | A | B | C |
| Isopropyl myristate | 20 g | 20 g | 20 g |
| Xanthan gum | 1.4 g | 1.4 g | 1.4 g |
| Ultramarines | 0.5 g | 0.5 g | 0.5 g |
| Magnesium oxide | 2.0 g | 2.0 g | 2.0 g |

| | Composition (bleaching paste) | | |
|---|---|---|---|
| | A | B | C |
| Sodium silicate | 15.0 g | 15.0 g | 15.0 g |
| Titanium dioxide | 1.0 g | 1.0 g | 1.0 g |
| 2-Oleamido-1,3-octadecanediol | 0.01 g | 0.01 g | 0.01 g |
| Magnesium stearate | 2.0 g | 2.0 g | 2.0 g |
| EDTA | 0.2 g | 0.2 g | 0.2 g |
| Sodium lauryl sulfate | 4.0 g | 4.0 g | 4.0 g |
| Silica | 2.5 g | 2.5 g | 2.5 g |
| Potassium persulfate | 39.08 g | 39.08 g | 39.08 g |
| Sodium persulfate | 6.0 g | 6.0 g | 6.0 g |
| Beeswax | 1.2 g | 1.2 g | 1.2 g |
| Liquid petroleum jelly | 1.0 g | 1.0 g | 1.0 g |
| Sodium salt of carboxymethyl starch | 2.5 g | 2.5 g | 2.5 g |
| Hydroxyethyl-2-nitro-para-toluidine | 1.6 g | — | — |
| 3-Methylamino-4-nitrophenoxyethanol | — | 1.6 g | — |
| Acid Red 87 | — | — | 1.6 g |

| Oxidizing composition | |
|---|---|
| Sodium stannate | 0.04 g |
| Pentasodium pentetate | 0.06 g |
| Cetearyl alcohol | 8.00 g |
| Ceteareth-33 | 2.00 g |
| 2-Phosphoric acid | qs pH = 3 |
| Hydrogen peroxide | 9.00 g |
| Tetrasodium pyrophosphate | 0.03 g |
| Water | 80.87 g |

Compositions A, B and C were each separately mixed, at the time of use, with the oxidizing composition in a bleaching paste/oxidizing composition ratio equal to 1/1.5.

The mixtures thus obtained were applied immediately and with a delay to a lock of natural grey hair containing 90% white hairs and to a lock of natural chestnut-brown hair, at a rate of 10 g of mixture per 1 g of hair. After a leave-on time of 30 minutes, the locks were rinsed, washed with a standard shampoo, rinsed again and then dried.

The tints obtained were described in the table below.

| Composition A | Natural grey hair containing 90% white hairs | Natural chestnut-brown hair |
|---|---|---|
| Immediate application | Deep coppery yellow | Golden coppery |
| Delayed application | Deep coppery yellow | Golden coppery |

| Composition B | Natural grey hair containing 90% white hairs | Natural chestnut-brown hair |
|---|---|---|
| Immediate application | Bright yellow | Golden |
| Delayed application | Bright yellow | Golden |

| Composition C | Natural grey hair containing 90% white hairs | Natural chestnut-brown hair |
|---|---|---|
| Immediate application | Pink | Orange coppery |
| Delayed application | Pink | Orange coppery |

It was found that the tints obtained were the same when the application was immediate and when it was delayed, which shows that the dyes were stable in the compositions in accordance with the present disclosure in the presence of hydrogen peroxide.

What is claimed is:

1. A composition for simultaneously bleaching and dyeing keratin fibers, comprising:
   at least one direct dye chosen from anionic dyes, nonionic dyes, and addition salts thereof, with the exception of 7-(6'-methyl-phenylazo)-1-acetamido-3,6-disulfo-8-hydroxynaphthalene, ortho-nitroanilines substituted meta to the amino group, quinoline and quinoline derivatives, and addition salts thereof;
and wherein said composition for simultaneously bleaching and dyeing keratin fibers further comprises
   at least one inert organic liquid;
   at least one peroxygenated salt; and
   at least one alkaline agent,
wherein the composition is anhydrous.

2. The composition according to claim 1, wherein the at least one anionic dye is chosen from acidic nitro direct dyes, acidic azo dyes, acidic azine dyes, acidic triarylmethane dyes, acidic indoamine dyes and acidic natural dyes.

3. The composition according to claim 2, wherein the at least one anionic dye is chosen from the following compounds:

| | |
|---|---|
| (C.I. 45380) | Acid Red 87 |
| (C.I. 10316) | Sodium salt of 2,4-dinitro-1-naphthol-7-sulfonic acid |
| (C.I. 10383) | Acid Orange 3 |
| (C.I. 13015) | Acid Yellow 9/Food Yellow 2 |
| (C.I. 14780) | Direct Red 45/Food Red 13 |
| (C.I. 13711) | Acid Black 52 |
| (C.I. 13065) | Acid Yellow 36 |
| (C.I. 14700) | Sodium salt of 1-hydroxy-2-(2',4'-xylyl-5-sulfonatoazo)naphthalene-4-sulfonic acid/Food Red 1 |
| (C.I. 14720) | Acid Red 14/Food Red 3/Mordant Blue 79 |
| (C.I. 14805) | Acid Brown 4 |
| (C.I. 15510) | Acid Orange 7/Pigment Orange 17/Solvent Orange 49 |
| (C.I. 15985) | Food Yellow 3/Pigment Yellow 104 |
| (C.I. 16185) | Acid Red 27/Food Red 9 |
| (C.I. 16230) | Acid Orange 10/Food Orange 4 |
| (C.I. 16250) | Acid Red 44 |
| (C.I. 17200) | Acid Red 33/Food Red 12 |
| (C.I. 15685) | Acid Red 184 |
| (C.I. 19125) | Acid Violet 3 |
| (C.I. 18055) | Sodium salt of 1-hydroxy-2-(4'-acetamidophenylazo)-8-acetamidonaphthalene-3,6-disulfonic acid/Acid Violet 7/Food Red 11 |
| (C.I. 18130) | Acid Red 135 |
| (C.I. 19130) | Acid Yellow 27 |
| (C.I. 19140) | Acid Yellow 23/Food Yellow 4 |
| (C.I. 20170) | 4'-(Sulfonato-2",4"-dimethyl)bis(2,6-phenylazo)-1,3-dihydroxybenzene/Acid Orange 24 |
| (C.I. 20470) | Sodium salt of 1-amino-2-(4'-nitrophenylazo)-7-phenylazo-8-hydroxynaphthalene-3,6-disulfonic acid/Acid Black 1 |
| (C.I. 23266) | (4-((4-Methylphenyl)sulfonyloxy)phenylazo)-2,2'-dimethyl-4-((2-hydroxy-5,8-disulfonato)naphthylazo)biphenyl/Acid Red 111 |

-continued

| | |
|---|---|
| (C.I. 27755) | Food Black 2 |
| (C.I. 25440) | 1-(4'-Sulfonatophenylazo)-4-((2"-hydroxy-3"-acetylamino-6",8"-disulfonato)naphthylazo)-6-sulfonatonaphthalene (tetrasodium salt)/Food Black 1 |
| (C.I. 42080) | 4-β-Hydroxyethylamino-3-nitrobenzenesulfonic acid |
| (C.I. 42090) | Acid Blue 9 |
| (C.I. 60730) | Acid Violet 43 |
| (C.I. 61570) | Acid Green 25 |
| (C.I. 62045) | Sodium salt of 1-amino-4-cyclohexylamino-9,10-anthraquinone-2-sulfonic acid/Acid Blue 62 |
| (C.I. 62105) | Acid Blue 78 |
| (C.I. 14710) | Sodium salt of 4-hydroxy-3-((2-methoxyphenyl)azo)-1-naphthalenesulfonic acid/Acid Red 4<br>2-Piperidino-5-nitrobenzenesulfonic acid<br>2-(4'-N,N-(2"-Hydroxyethyl)amino-2'-nitro)-anilinethanesulfonic acid<br>4-β-Hydroxyethylamino-3-nitrobenzenesulfonic acid |
| (C.I. 42640) | Acid Violet 49 |
| (C.I. 42080) | Acid Blue 7<br>Acid Blue 156<br>Acid Blue 317 |
| (C.I. 58005) | Sodium salt of 1,2-dihydroxy-3-sulfoanthraquinone/ Mordant Red 3 |
| (C.I. 62055) | Sodium salt of 1-amino-9,10-dihydro-9,10-dioxo-4-(phenylamino)-2-anthracenesulfonic acid/Acid Blue 25 |
| (C.I. 14710) | Sodium salt of 4-hydroxy-3-((2-methoxyphenyl)azo)-1-naphthalenesulfonic acid/Acid Red 4. |

4. The composition according to claim 1, wherein the at least one nonionic dye is chosen from nonionic nitrobenzene dyes, nonionic azo, azomethine, methine, anthraquinone, naphthoquinone, benzoquinone, phenothiazine, indigoid, xanthene, phenanthridine, phthalocyanin and triarylmethane-based dyes.

5. The composition according to claim 4, wherein the at least one nonionic dye is chosen from 1-hydroxy-3-nitro-4-N-(γ-hydroxypropyl)aminobenzene;
N-(β-hydroxyethyl)amino-3-nitro-4-aminobenzene;
1 hydroxy-3-nitro-4-N-(β-hydroxyethyl)aminobenzene; 1,4-diamino-2-nitrobenzene;
1-amino-2-nitro-4-methylaminobenzene; N(β-hydroxyethyl)-2-nitro-para-phenylene-diamine; 2-nitro-4-aminodiphenylamine; 1-amino-3-nitro-6-hydroxybenzene;
1-(β-aminoethyl)amino-2-nitro-4-(β-hydroxyethyloxy) benzene;
1-(β,γ-dihydroxypropyl)oxy-3-nitro-4-(β-hydroxyethyl) aminobenzene;
1-hydroxy-3-nitro-4-aminobenzene; 1-hydroxy-2-amino-4,6-dinitrobenzene;
1-methoxy-3-nitro-4-(β-hydroxyethyl)aminobenzene; 2-nitro-4'-hydroxydiphenylamine;
1-(β-hydroxyethyl)amino-2-methoxy-4-nitrobenzene; 1-amino-2-nitro-6-methylbenzene;
1-(β-hydroxyethyl)amino-2-hydroxy-4-nitrobenzene;
N-(β-hydroxyethyl)-2-nitro-4-trifluoromethylaniline;
4-(β-hydroxyethyl)amino-3-nitrochlorobenzene; 4-(β-hydroxy-ethyl)amino-3-nitromethylbenzene; 4-(β,γ-dihydroxypropyl)amino-3-nitrotrifluoromethyl-benzene;
1-(β-ureidoethyl)amino-4-nitrobenzene; 1-hydroxy-2-amino-5-nitrobenzene;
1-amino-2-[tris(hydroxymethyl)methyl]amino-5-nitrobenzene; 1-(β-hydroxyethyl)-amino-2-nitrobenzene; 4-(β-hydroxyethyl)amino-3-nitrobenzamide; 1-β-hydroxyethyl)-amino-4-N,N-bis(β-hydroxyethyl)amino-2-nitrobenzene; 1-(γ-hydroxypropyl)-amino-4-N,N-bis (β-hydroxyethyl)amino-2-nitrobenzene; 1-(β-hydroxyethyl)-amino-4-(N-methyl-N-β-hydroxyethyl) amino-2-nitrobenzene; 1-β-hydroxyethyl)-amino-4-(N-ethyl-N-β-hydroxyethyl)amino-2-nitrobenzene;
1-(β,γ-dihydroxy-propyl)amino-4-(N-ethyl-N-β-hydroxyethyl)amino-2-nitrobenzene; Disperse Orange 3; Disperse Red 17; Disperse Violet 4; Disperse Violet 8; Disperse Blue 1; Disperse Red 15; Solvent Violet 13; Solvent Violet 11; Disperse Blue 3; Disperse Blue 7; Disperse Red 11; Natural Brown 7; Disperse Black 9; Disperse Violet 15; Natural Orange 6;
2-hydroxy-3-methoxy-1,4-naphthoquinone; 3-hydroxy-2-methyl-1,4-naphthoquinone or phthiocol; 3,6-dihydroxy-5-methoxy-p-toluquinone or spinulosin; and HC Blue 14.

6. The composition according to claim 1, wherein the at least one direct dye is present in an amount ranging from 0.0001% and 10% by weight, relative to the total weight of the composition.

7. The composition according to claim 1, wherein the at least one inert organic liquid is chosen from polydecenes of formula $C_{10n}H_{[(20n)+2]}$ wherein n ranges from 3 to 9, esters of fatty alcohols and of fatty acids, sugar esters and diesters of $C_{12}$-$C_{24}$ fatty acids, cyclic ethers and cyclic esters, silicone oils, mineral oils and plant oils.

8. The composition according to claim 7, wherein the at least one inert organic liquid is chosen from polydecenes of formula $C_{10n}H_{[(20n)+2]}$ wherein n ranges from 3 to 9, and esters of fatty alcohols and of fatty acids.

9. The composition according to claim 1, wherein the at least one inert organic liquid is present in an amount ranging from 5% to 60% by weight, relative to the total weight of the composition.

10. The composition according to claim 1, wherein the at least one peroxygenated salt is chosen from alkali metal and alkaline-earth metal persulfates, perborates, percarbonates and peroxides.

11. The composition according to claim 10, wherein the at least one peroxygenated salt is chosen from persulfates.

12. The composition according to claim 11, wherein the at least one peroxygenated salt is chosen from sodium persulfate, potassium persulfate and ammonium persulfate.

13. The composition according to claim 1, wherein the at least one peroxygenated salt is present in an amount ranging from 1% to 70% by weight, relative to the total weight of the composition.

14. The composition according to claim 1, wherein the at least one alkaline agent is chosen from urea, ammonium chloride, ammonium sulfate, ammonium phosphate, ammonium nitrate, and alkali metal and alkaline-earth metal silicates, phosphates and carbonates.

15. The composition according to claim 1, wherein the at least one alkaline agent is present in an amount ranging from 0.01% to 40% by weight, relative to the total weight of the composition.

16. A process for simultaneously bleaching and dyeing keratin fibers, comprising
applying at least one anhydrous composition for simultaneously bleaching and dyeing to the keratin fibers in the presence of at least one aqueous composition optionally comprising hydrogen peroxide,
wherein the at least one anhydrous composition for simultaneously bleaching and dyeing comprises:
at least one direct dye chosen from anionic dyes, nonionic dyes, and addition salts thereof, with the exception of 7-(6'-methyl-phenylazo)-1 acetamido-3,6-disulfo-8-hydroxynapthalene, ortho-nitroanilines substituted meta to the amino group, quinoline and quinoline derivatives, and addition salts thereof;
at least one inert organic liquid;
at least one peroxygenated salt; and
at least one alkaline agent.

17. A multi-compartment device, comprising at least two compartments each containing compositions, the mixing of which leads to an aqueous composition comprising:

at least one direct dye chosen from anionic dyes, nonionic dyes, and addition salts thereof, with the exception of 7-(6'-methyl-phenylazo)-1-acetamido-3,6-disulfo-8-hydroxynaphthalene, ortho-nitroanilines substituted meta to the amino group, quinoline and quinoline derivatives, and addition salts thereof;

at least one inert organic liquid;

at least one peroxygenated salt; and at least one alkaline agent wherein at least one of said compositions is anhydrous.

* * * * *

UNITED STATES PATENT AND TRADEMARK OFFICE
CERTIFICATE OF CORRECTION

PATENT NO. : 7,736,395 B2  Page 1 of 1
APPLICATION NO. : 11/476814
DATED : June 15, 2010
INVENTOR(S) : Sylvain Kravtchenko It is certified that error appears in the above-identified patent and that said Letters Patent is hereby corrected as shown below:

Claim 5, column 13, line 39, "N(β-hydroxyethyl)" should read -- N-(β-hydroxyethyl) --.

Signed and Sealed this

Twenty-fourth Day of August, 2010

David J. Kappos
*Director of the United States Patent and Trademark Office*